United States Patent [19]

Takeuchi et al.

[11] Patent Number: 4,519,959
[45] Date of Patent: May 28, 1985

[54] GAS-LIQUID CONTACTING APPARATUS

[76] Inventors: Tatsuro Takeuchi, 60-38, Miyake-cho, Moriyama, Shiga 524; Shohei Yoshida, 2-1, Aza-higashiyashiki, Yamada, Itami, Hyogo 664; Kazuhiro Kawai, 201 Takeda Yakuhin Seiunryo, Mitsui-morigatao, Hikari, Yamaguchi 743, all of Japan

[21] Appl. No.: 484,552

[22] Filed: Apr. 13, 1983

[30] Foreign Application Priority Data

Apr. 14, 1982 [JP] Japan ................................. 57-62917
Feb. 10, 1983 [JP] Japan ................................. 58-20774

[51] Int. Cl.³ .............................................. B01F 3/04
[52] U.S. Cl. ..................... 261/93; 261/36 R; 261/152; 366/102; 366/103; 366/316; 422/227; 422/228; 422/231; 435/314; 435/315; 435/316
[58] Field of Search ............... 261/93, 87, 91, 36 R, 261/152; 435/313–315; 366/102–104, 316; 422/227, 228, 231; 252/361; 209/169, 170; 210/219, 221.2

[56] References Cited

U.S. PATENT DOCUMENTS

| | | | |
|---|---|---|---|
| 2,141,047 | 12/1938 | Schulte | 261/93 |
| 2,673,724 | 3/1954 | Potts | 261/87 |
| 3,625,834 | 12/1971 | Muller | 261/93 X |
| 3,650,513 | 3/1972 | Werner | 261/87 |
| 3,815,879 | 6/1974 | Mikhailov et al. | 261/93 |
| 3,847,750 | 11/1974 | Ridgway, Jr. et al. | 435/315 |
| 3,962,042 | 6/1976 | Malick | 435/315 X |
| 3,986,934 | 10/1976 | Muller | 435/315 X |
| 4,243,636 | 1/1981 | Shiraki et al. | 422/228 X |

FOREIGN PATENT DOCUMENTS

| | | | |
|---|---|---|---|
| 51-10178 | 1/1976 | Japan | 261/93 |
| 1424728 | 2/1976 | United Kingdom | 261/93 |
| 1455311 | 11/1976 | United Kingdom | 261/93 |

OTHER PUBLICATIONS

"Progress in Industrial Microbiology", vol. III, D. J. D. Hockenhull, London, 1961.

Primary Examiner—Richard L. Chiesa

[57] ABSTRACT

A gas-liquid contacting apparatus is constituted by an upright vessel, at least one perforated gas distributor for supplying a gaseous medium into a liquid medium within the vessel, a plate-like rotary disintegrator positioned within the vessel and above the gas distributor for disintegrating bubbles of the gaseous medium into fine bubbles, and a drive shaft concentrically extending through the vessel for the support of the rotary disintegrator.

20 Claims, 28 Drawing Figures

GAS-LIQUID CONTACTING APPARATUS

This invention generally relates to a gas-liquid contacting apparatus suited for use in carrying out a chemical process including, for example, fermentation and gas-liquid reaction and, more particularly, to a gas-liquid contacting apparatus for agitating a liquid medium by the utilization of bubbles of gaseous medium.

The term "liquid" or "liquid medium" hereinabove and hereinafter referred to is to be understood as a liquid or liquid medium either with or without solid particles suspended therein.

The British Patent Specification No. 1,455,311, published Nov. 10, 1976 discloses a gas-liquid contacting apparatus of a construction reproduced in FIG. 1 of the accompanying drawings. Referring to FIG. 1, the apparatus comprises an upright bubble column or vessel 10, a perforated ring pipe 12 disposed within the vessel 10 adjacent the bottom thereof for supplying a gaseous medium into the vessel 10 so as to disperse it in a quantity of liquid medium within the vessel 10 in the form of bubbles, a rotary disintegrator in the form of a micro-mixing 14 disposed within the vessel 10 above the perforated ring pipe 12 for mixing and disintegrating ascending bubbles of the gaseous medium into fine bubbles, and a defoaming nozzle 16 disposed within the vessel 10 adjacent the top thereof for spraying that portion of the liquid medium which has been circulated through a circulating line 18 by way of a pump 20 and a heat-exchanger 22, onto the top level of the liquid medium within the vessel 10 for defoaming.

The micro-mixing vane 14 is disclosed as comprising a plurality of elongated blades extending radially outwardly from a drive shaft 24 and spaced an equal angle from each other about the drive shaft 24, each of said blades having a plurality of equally spaced wires which are rigidly mounted on the respective blade so as to extend at right angles thereto and in a direction either parallel or transverse to the longitudinal axis of the vessel 10. An alternative form of the micro-mixing vane 14 is also disclosed as comprising a plurality of wire mesh blades extending radially outwardly from the drive shaft 24 and spaced an equal angle from each other about the drive shaft 24 and oriented in parallel to the longitudinal axis of the vessel 10.

While the pattern of flow of the bubbled liquid medium occurring within the vessel may generally be considered as divided into a gentle circulation flow occurring in a major portion within the vessel and a localized turbulent flow in which the liquid medium and the bubbles of the gaseous medium are vigorously mixed together, the gas-liquid contacting apparatus according to this British reference is so designed that both the circulation flow and the localized turbulent flow can be induced simultaneously by the rotation of the micro-mixing vane 14. Because of this design, it has been found difficult to establish the circulation flow and the turbulent flow in well balanced condition and, in order to accomplish this, an increased amount of energy is required to drive the micro-mixing vane and the efficiency is consequently reduced. In other words, the rotation of the micro-mixing vane by itself is unable to effectively provide energies sufficient to induce both the circulation flow and the turbulent flow. By way of example, where the vessel is used as a fermentation tank in which fermentation takes place with the aid of oxygen, and when the speed of rotation of the micro-mixing vane is excessively increased to accelerate the oxygen transfer, the circulation takes place at a higher rate than necessary and unnecessarily increased energy is consequently consumed. In the case where the liquid medium charged in the vessel is a high viscosity medium, a relatively gentle agitation is required for such high viscosity medium and, therefore, the energy necessary to induce the turbulent flow tends to be short of the required amount, resulting in that the oxygen transfer cannot take place at a required speed.

This tends to constitute a cause of bacterial contamination where the gas-liquid contacting apparatus is used as, for example, a fermentation tank, and therefore, is not desirable. Moreover, according to the known method, not all of the bubbles will be disintegrated into fine bubbles, some of them ascending without being disintegrated. This is a phenomenon which can be observable when bubbles adhere to the micro-mixing vane, and which often occurs particularly when the rate of supply of the gaseous medium into the vessel is increased.

Accordingly, this invention has been developed with a view to substantially eliminating the above discussed disadvantages and inconveniences inherent in the prior art gas-liquid contacting apparatus and has for its essential object to provide an improved gas-liquid contacting apparatus wherein the bubbles of the gaseous medium supplied into the vessel can be effectively disintegrated into fine bubbles by the rotation of the rotary disintegrator with minimized power consumption.

Another important object of this invention is to provide an improved gas-liquid contacting apparatus of the type referred to above, wherein a sealed bearing for the rotary disintegratory is provided which does not contact the liquid medium within the vessel. However, where the sealed bearing is submerged in the liquid medium, a drive unit for driving the rotary disintegrator may be arranged beneath the vessel.

In order to accomplish these objects, this invention provides an improved gas-liquid contacting apparatus which comprises an upright vessel for accommodating a quantity of liquid medium therein, at least one perforated gas distributor disposed within the vessel for supplying a gaseous medium under pressure into the vessel so as to disperse into the liquid medium in the form of bubbles, at least one generally disc-shaped rotary disintegrator disposed concentrally within the vessel above the perforated gas distributor and having a plurality of apertures defined in an outer peripheral region thereof so as to extend completely through the thickness of the rotary disintegrator, said rotary disintegrator having a diameter sufficient to define an annular clearance between the periphery thereof and the inner wall surface of the vessel, and a drive shaft drivingly coupled with a drive unit for rotating the rotary disintegrator in a plane perpendicular to the longitudinal axis of the vessel.

In this construction, when the rotary disintegrator is rotated in one direction together with the drive shaft, the rotary disintegrator disintegrates the bubbles, then ascending from the gas distributor upwards in the vessel across the apertures in the rotary disintegrator, into fine bubbles to enhance the contact between the liquid medium and the gaseous medium within the vessel.

According to this invention, a baffling means may be arranged within the vessel above the rotary disintegrator for disturbing, i.e., providing a resistance to, the whirling flow of the liquid medium.

The vessel used in this invention may have either a circular cross-section or a polygonal cross-section approximating a circular shape.

The perforated gas distributor may comprises a perforated piping having a gas supply piping extending from the perforated piping to a source of the gaseous medium exteriorly of the vessel. The gas supply piping may either extend through the side wall or the bottom wall of the vessel or may be inserted into the vessel from the top. While the perforated piping within the vessel is preferably positioned adjacent the bottom of the vessel, it may be positioned substantially intermediately of the height of the vessel provided that it is submerged in the liquid medium within the vessel and located below the rotary disintegrator. The perforated piping may be in the form of a ring pipe, a straight tube, a coiled tube or of any other suitable shape provided that the supply of the gaseous medium into the vessel can be centered immediately below a central region of the rotary disintegrator.

The rotary disintegrator positioned immediately above the perforated piping of the gas distributor is constituted by a flat plate of either circular configuration or polygonal configuration approximating a circular shape and may have a bearing boss or reinforcement formed thereon in concentric relation thereto. The rotary disintegrator has its outer peripheral region provided with the apertures extending completely through the thickness thereof for the passage of bubbled liquid medium therethrough as the bubbles of the gaseous medium emerging from the perforated piping into the vessel ascend in the vessel. The aperture so defined in the outer peripheral region of the rotary disintegrator may be a through-hole of any suitable configuration, for example, circular, triangular, square or rectangular shape, slots or slits cut radially inwardly from the peripheral edge of the rotary disintegrator and spaced an equal distance from each other about the axis of rotation of the rotary disintegrator.

The number of the apertures in the rotary disintegrator as well as the size of each of the apertures may be determined in consideration of the rate of discharge of the gaseous medium into the vessel, physical properties such as, for example, the density and the viscosity, of the liquid medium and/or other factors. However, the ratio of the total surface area of the rotary disintegrator relative to the sum of respective surface areas of the apertures in the rotary disintegrator is preferably within the range of 0.05 to 0.35 in view of the fact that, if the sum of the respective surface areas of the apertures is too small, portion of the gaseous medium discharged into the liquid medium within the vessel will, in the form of bubbles, pass upwards through the annular clearance between the periphery of the rotary disintegrator and the inner wall surface of the vessel without being disintegrated into fine bubbles by the rotary disintegrator on the one hand and that, if it is too large, the liquid medium tends to be stirred along with the disintegration of the bubbles into the fine bubbles, requiring an increased drive to rotate the rotary disintegrator on the other hand.

The undersurface of the rotary disintegrator facing the bottom of the vessel must be a planar surface such that, during the rotation of the rotary disintegrator, the bubbles floating beneath the rotary disintegrator can form a vortex.

The number of sets of the gas distributor and the rotary disintegrator need not be limited to one, but two or more sets of the gas distributor and the rotary disintegrator may be employed, in which case the sets may be arranged either one above the other or in side-by-side relation.

Moreover, according to this invention, the vessel may have a stirring means, including a draft tube disposed concentrically above the rotary disintegrator within the vessel and a blade stirrer disposed within or adjacent the draft tube, for circulating the liquid medium exteriorly and interiorly of the draft tube. Since the rotary disintegrator itself has so small a thickness that the cross-sectional surface area of each of the apertures taken in a direction perpendicular to the plane of rotation thereof is small, the rotary disintegrator, when rotated, does not produce so much agitation as to be likely to result in the circulation of the liquid medium, but causes the bubbles of the gaseous medium present beneath the rotary disintegrator to be formed into a vortex and then to be disintegrated into fine bubbles as they ascend exteriorly of the vortex and upwardly through the apertures in the rotary disintegrator, thereby establishing a localized turbulent flow. In view of the fact that the circulation flow which is a uni-directional flow whose streamlines do not intersect in a complex manner, is effective to cause the finely disintegrated bubbles and, if any, solid particles contained in the liquid medium to be uniformly dispersed in the liquid medium, it is the combination of the draft tube and the stirrer blade that produces the circulation flow within the vessel. Specifically, the draft tube is disposed concentrically within the vessel and positioned above the rotary disintegrator in spaced relation thereto while the stirrer blade is operatively arranged within or adjacent the draft tube. In this arrangement, when and so long as the stirrer blade is rotated, the liquid medium within the vessel is circulated exteriorly and interiorly of the draft tube thereby to disperse the bubbles and the solid particles uniformly in the liquid medium. Preferably, the draft tube is supported in position within the vessel with its upper end held generally level with the top level of the liquid medium within the vessel so that the circulation flow of the liquid medium induced by the draft tube can pitch onto and, therefore, defoam the foams floating on the top level of the liquid medium, which foams would otherwise hamper the uniform and thorough gas-liquid contact. In view of the foregoing, by the employment of the simple arrangement of the draft tube and the stirrer blade, the previously described object of this invention can effectively be accomplished with the substantial elimination of the disadvantages inherent in the prior art. Where the apparatus of this invention is used as a fermentation tank, the oxygen dispersion can advantageously be accelerated so as to achieve accelerated fermentation and also increased concentration of the substrate. In addition, any troubles resulting from the presence of the foams can also be minimized which results in an increased charge efficiency and therefore increased productivity.

These and other objects and features of this invention will become clear from the following detailed description of preferred embodiments thereof with reference to the accompanying drawings, in which.

Before the description of this invention proceeds, it is to be noted that like parts are designated by like reference numerals throughout the accompanying drawings except for FIG. 1.

FIRST EMBODIMENT (FIGS. 2 TO 10)

Figure 1:
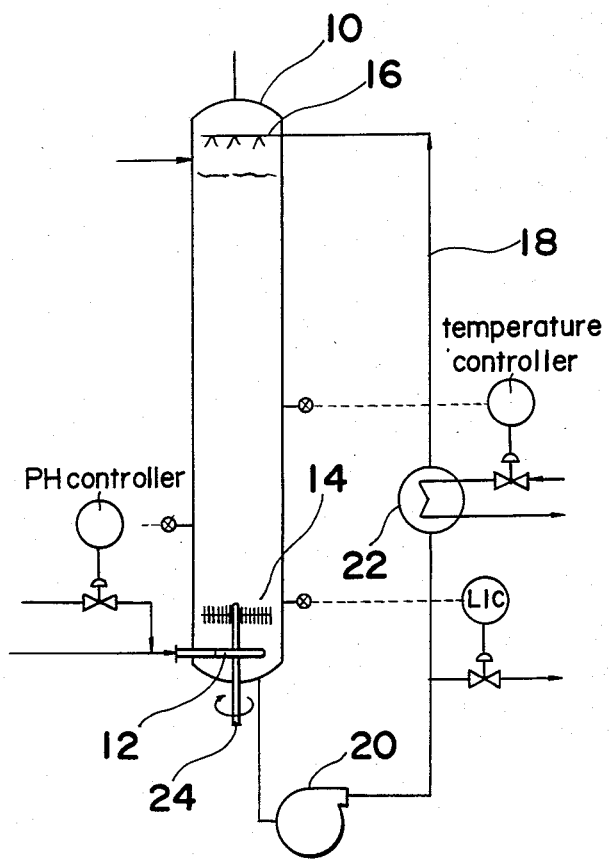
FIG. 1 is a schematic diagram showing the prior art gas-liquid contacting apparatus.

Referring first to FIGS. 2 to 5, the gas-liquid contacting apparatus according to a first preferred embodiment of this invention comprises a generally cylindrical upright vessel 30 for accommodating therein a quantity of liquid medium L, a perforated ring pipe 32 for supplying compressed air into the liquid medium L, a rotary disintegrator 34 in the form of a disc-shaped thin plate having a plurality of apertures 36 defined therein as will be described later, a coiled tube 38 for the passage of a coolant therethrough for adjusting the temperature of the liquid medium L, and a plurality of equally spaced bubble plates 40 for guiding the liquid medium containing bubbles of the compressed air.

The vessel 30 is in the form of a cylindrical upright tank adapted to accommodate the liquid medium in a quantity occupying about, for example, 80% of the height H of the vessel 30. The vessel 30 has its top end closed by a lid 42. The coiled tube 38 may also be used for the passage of a heating medium therethrough for heating the liquid medium within the vessel 30. The interior of the vessel 30 is communicated to the atmosphere through an opening 44 in the lid 42. The bottom of the vessel 30 has a drain opening 46 communicated through a shut-off valve 48 to any suitable receptacle positioned beneath the vessel 30.

The perforated ring pipe 32 is laid horizontally in parallely spaced relation to the bottom of the vessel 30 so that the compressed air or inert gas fed from a source 50 of compressed gaseous medium through a flow regulator 52 can be discharged into the liquid medium L generally concentrically from below in the form of bubbles.

Figure 3:
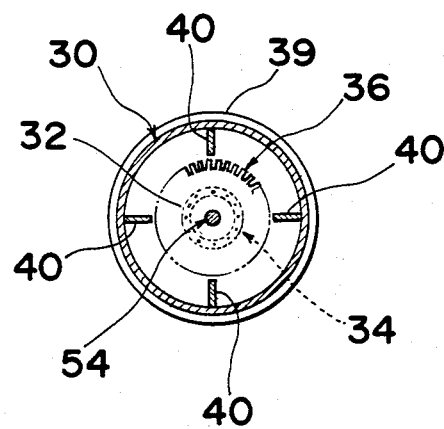
FIG. 3 is a cross-sectional view taken along the line III—III in FIG. 2.
Figure 4:
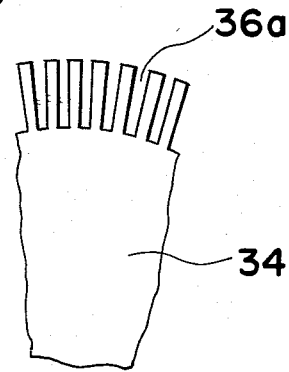
FIG. 4 is a fragmental plan view, taken on an enlarged scale, of a portion of a rotary disintegrator used in the apparatus of FIG. 2.

The rotary disintegrator 34 is in the form of a disc-shaped thin flat plate supported in a manner as will be described later for rotation within the vessel 30 in a plane perpendicular to the longitudinal axis of the vessel 30. As best shown in FIGS. 3 and 4, the apertures 36 defined in the rotary disintegrator 34 are in the form of slits 36a cut radially inwardly from the periphery of the rotary disintegrator 34 and spaced an equal angle from each other about the axis of rotation of the rotary disintegrator 34. The rotary disintegrator 34 is mounted on a drive shaft 54 for rotation together therewith, which shaft 54 extends rotatably through a bearing 56 rigidly carried by the bottom plate of the vessel 30 in coaxial relation to said vessel 30 and is drivingly coupled to a drive motor M through a torque meter T. The bearing 56 has a mechanical seal 57 effective to avoid any possible leakage of the liquid medium L to the outside of the vessel 30 through the bearing 56. Preferably, the drive system including the motor M and the drive shaft 54 is so designed that the rotary disintegrator 34 can be rotated in one direction at a rate within the range of 600 to 800 rpm. The rotary disintegrator 34 has a diameter sufficient to allow an annular clearance of a predetermined width to be defined between the periphery thereof and the inner wall surface of the vessel 30 so that, when and so long as the rotary disintegrator 34 is rotated together with the shaft 54 about the axis of the shaft, the bubbles of the gaseous medium discharged from the perforated ring pipe 32 into the liquid medium can spread radially outwards below the rotary disintegrator 34 while forming a vortex beneath the rotary disintegrator 34 and then ascend through the apertures 36 towards the top of the vessel 30. During the rotation of the rotary disintegrator 34, two currents are produced, one current flowing upwards through the apertures 36 in the rotary disintegrator 34 and the other flowing downwards through the annular clearance between the periphery of the rotary disintegrator 34 and the inner wall surface of the vessel 30, and the downwardly flowing current subsequently adjoins the bubbles of the gaseous medium, which then form the vortex beneath the rotary disintegrator 34, and is then forced to pass upwardly through the apertures 36 in the rotary disintegrator 34 together with the bubbles. At the same time, with the rotary disintegrator 34 being rotated at a high speed, the bubbles passing upwardly through the apertures 36 are successively sheared by the peripheral lip regions of the rotary disintegrator 34 confronting the respective apertures 36 and thus disintegrated into fine bubbles, which in turn float further upwards in the liquid medium L.

In any event, the requirements for the rotary disintegrator 34 to satisfy will be summarized as follows.

Although in the foregoing description the rotary disintegrator 34 has been described as having a disc shape, it may have a polygonal shape if it approximates generally the circular shape. In either case, at least the undersurface of the rotary disintegrator 34 confronting the bottom of the vessel 30 must be flat for the vortex of the bubbles to be formed beneath the rotary disintegrator 34. Moreover, in order for the rotary disintegrator 34 not to agitate the liquid medium during the rotation thereof, the outer peripheral portion of the rotary disintegrator 34 where the apertures 36 are defined must be as thin as possible and must have no indents of any shape which would likely to result in agitation of the liquid medium during the rotation of the rotary disintegrator 34.

Figure 5:
FIG. 5 is a cross-sectional view of the disintegrator of FIG. 4.
Figure 6:
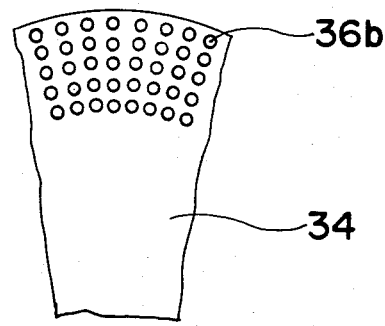
FIG. 6 is a view similar to FIG. 4, showing an alternative form of the rotary disintegrator.

In addition to the slits 36a shown in FIGS. 3 to 5, the apertures 36 may be in the form of equally spaced radial rows of a plurality of through-holes 36b as shown in FIG. 6. In either case, the ratio of the total surface area of the rotary disintegrator relative to the sum of respective surface areas of the apertures 36, which ratio is hereinafter referred to as the opening ratio, is preferably within the range of 0.05 to 0.35. In addition, the neighbouring apertures 36 are spaced a predetermined angle within the range of 1° to 10° with respect to the axis of rotation of the rotary disintegrator 34 while the size of each aperture 34, that is, the width in the case of the slits 36a or the diameter in the case of the through-holes 36b, is not larger than 20 mm and preferably not larger than 10 mm. Moreover, the outer peripheral portion of the rotary disintegrator 34 in which the apertures 36 are defined must have a width, as measured in the radial direction of the rotary disintegrator 34, which is half the radius of the rotary disintegrator 34. When in use, the rotary disintegrator 34 must be rotated at such a speed that the radial innermost end of each slit 36a or the radial innermost one of the through-holes 36b of each radial row can angularly move at a velocity of about 5 m/sec or higher, which is hereinafter referred to as the inner peripheral velocity.

The baffle plates 40 are in the form of elongated flat plates of generally narrow width secured at one side edge to the inner wall surface of the vessel 30 so as to protrude radially inwardly within the vessel 30 while spaced an equal angle from each other in the circumferential direction of the vessel 30. It is to be noted that each of the baffle plates 40 extends longitudinally of the vessel 30 with its upper and lower ends spaced a distance beneath the top surface level S of the liquid medium within the vessel 30 and a distance above the rotary disintegrator 34. Accordingly, the baffle plates 40 so arranged as hereinabove described are effective to avoid the occurrence of any possible whirling of the liquid medium L circumferentially along the inner wall surface of the vessel 30 and also to induce a rectified flow of the liquid medium in a direction longitudinally of the vessel 30.

In the gas-liquid contacting apparatus of the construction described hereinbefore, when the rotary disintegrator 34 is rotated at the high speed with the liquid medium L filling the vessel 30 while, at the same time, the gaseous medium under pressure is supplied into the liquid medium from the perforated ring pipe 32, the two currents, i.e., the ascending current moving upwardly through the apertures 36 and the descending current moving through the annular clearance between the rotary disintegrator 34 and the inner wall surface of the vessel 30, are produced as hereinbefore described. By the action of these currents, the bubbles of the gaseous medium discharged into the liquid medium immediately below the central region of the rotary disintegrator 34 join the descending current which is in turn deflected to flow upwards to allow the bubbles to move upwardly through the apertures 36 in the rotary disintegrator 34 being rotated. As the bubbles move upwards through the apertures 36, they are sheared and, therefore, disintegrated into fine bubbles and the liquid medium containing the finely divided bubbles is forced to flow upwards in the form of a rectified stream without being whirled by the presence of the baffle plates 40.

In one example, the vessel 30 is 145 mm in inner diameter (about 165 cm$^2$ in transverse sectional surface area) and 1,000 mm in height. A quantity of the liquid medium is placed in the vessel 30 with its top surface level at 80% of the height H. The ring pipe 32, 5 mm in diameter and formed by bending a 50 mm perforated pipe into a circular shape, is arranged generally in parallel relation to the bottom of the vessel 30 with the perforations in the ring pipe 32 oriented upwards. In this construction, when the gaseous medium is discharged from the ring pipe 32 into the liquid medium at a rate of 1 VVM, a superficial gas velocity of 1.05 cm/sec and a mean gas retention time of about 6 sec can be attained. The rotary disintegrator 34 positioned above the perforated ring pipe 32 is a disc, 3 mm in thickness and 100 mmm in diameter, and is arranged within the vessel 30 generally in parallel relation to the bottom of the vessel 30. The annular clearance so formed between the periphery of the rotary disintegrator 34 and the inner wall surface of the vessel 30 is, therefore, 22.5 mm in width (and 86.5 cm$^2$ in total surface area). As the apertures 36 in the rotary disintegrator 34 in the case where the latter has an outer diameter RO within the range of 100 to 140 mm, the slits as shown in FIG. 4, 10 to 14 mm in length and 2 to 3 mm in width, are employed and are spaced a pitch of 4 to 7 mm from each other. In this case the sum of the surface areas occupied by the slits 36a is 14.4 to 14.8 cm$^2$ against 78.5 to 154 cm$^2$ for the total surface area of the rotary disintegrator 34. When the rotary disintegrator is rotated at an inner peripheral velocity of 5.65 to 5.86 m/sec, the superficial gas velocity of the bubbles moving upwardly through the slits 36a can be caused to be within the range of 11.7 to 12.0 cm/sec.

In the case where the through-holes 36b shown in FIG. 6 are employed for the apertures 36 in the rotary disintegrator 34 having an outer diameter RO within the range of 100 to 140 mm, the through-holes 2.0 to 3.0 mm in diameter should be spaced a pitch of 3.5 to 4.5 mm from each other and at a pitch angle $\theta$ of 4° to 5° about the axis of rotation of the rotary disintegrator 34.

Figure 8:
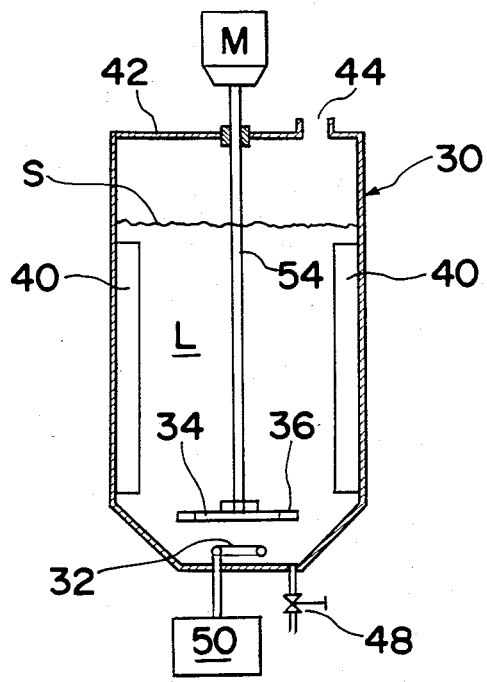
FIGS. 8 to 10 are schematic longitudinal sectional views, showing respective modified forms of the apparatus of FIG. 2.

The number of the baffle plates 40 employed is four and each baffle plate, 700 mm in length, 27.5 mm in width and 3 mmm in thickness, is secured at one side edge to the inner wall surface of the vessel 30 in parallel relation to the longitudinal axis thereof with its lower end spaced 34 mm upwardly from the level of the rotary disintegrator 34. It is to be noted that the rotary disintegrator 34 is mounted on the drive shaft 54 extending concentrically through the ring pipe 32 and then sealedly and rotatably through the bearing 56 mounted coaxially on the bottom wall of the vessel 30, which drive shaft 54 is in turn coupled to the electric drive motor M positioned exteriorly of the vessel 30. If the electric motor M is supported above the vessel 30 with the drive shaft extending downwards therefrom towards the bottom of the vessel 30 as shown in FIG. 8, the use of the bearing 54 for sealedly and rotatably supporting the drive shaft can be omitted. One or both of the coiled tube 38 and the jacket 39 may not be always necessary. Moreover, a lower portion of the wall forming the vessel 30 adjacent the rotary disintegrator 34 may be tapered downwards towards the bottom wall of the vessel 30 as shown in FIG. 8. Furthermore, as shown in FIG. 10, in the case where the drive shaft 54 extends downwards into the vessel 30 from the motor M, the lower end of the drive shaft 54 may be rotatably coupled to the bearing 56 positioned inside the vessel 30 and rigidly mounted on the bottom wall of the vessel 30, as shown in FIG. 9.

Figure 9:
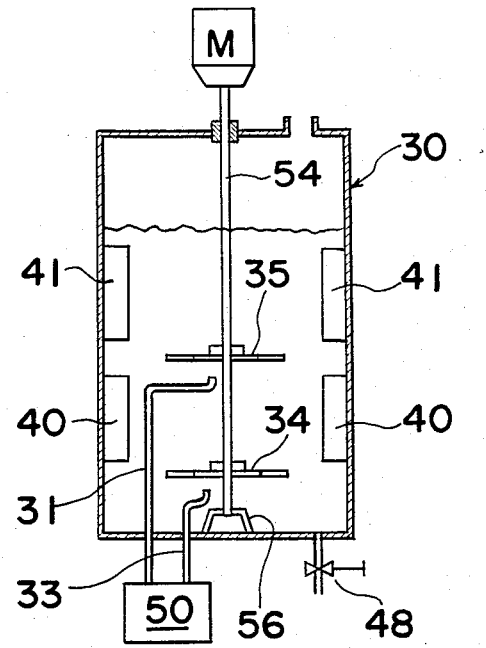
Figure 10:
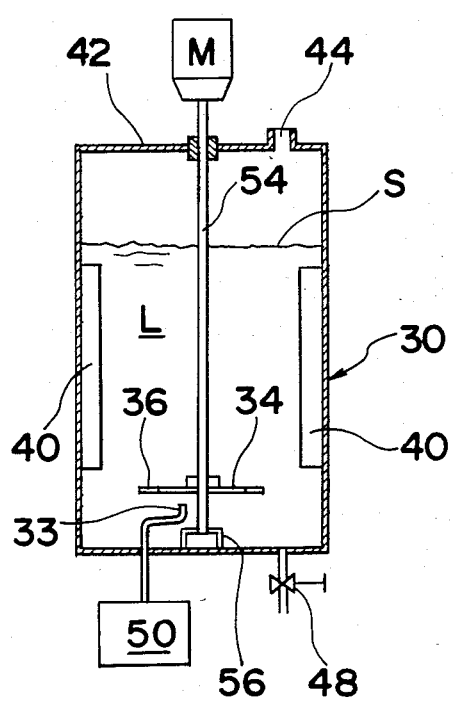
Figure 11:
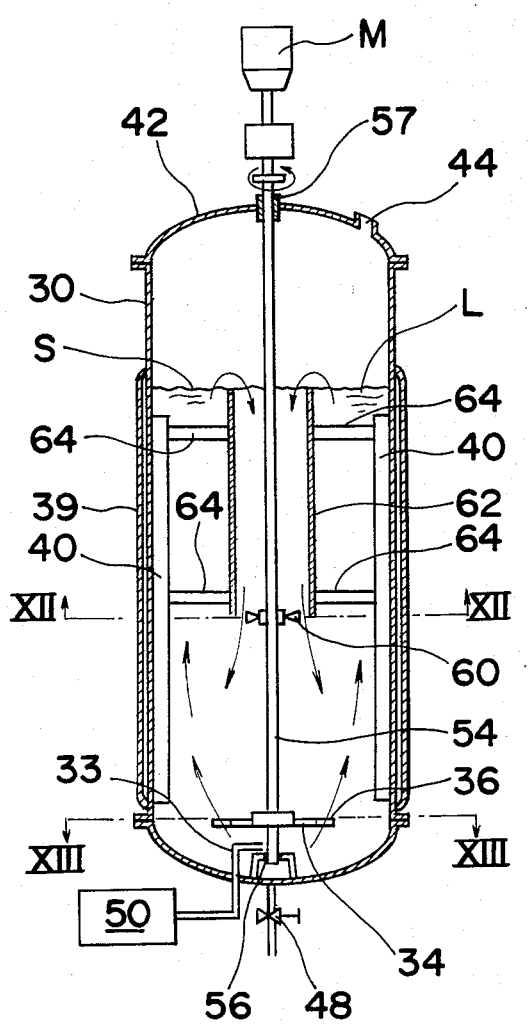
FIG. 11 is a view similar to FIG. 2, showing the apparatus according to a second embodiment of this invention.
Figure 12:
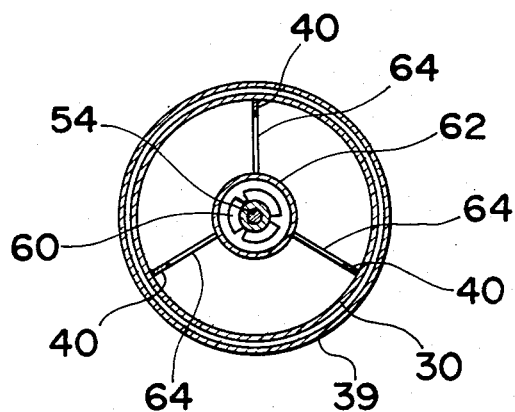
FIG. 12 is a cross-sectional view taken along the line XII—XII in FIG. 11.
Figure 13:
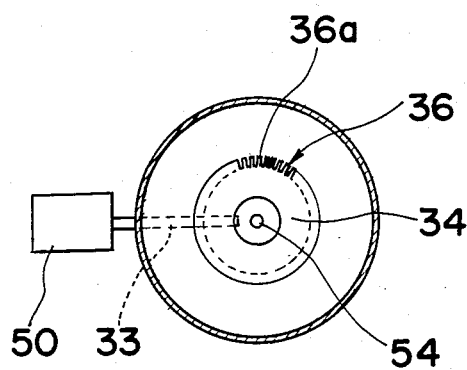
FIG. 13 is a cross-sectional view taken along the line XIII—XIII in FIG. 11.
Figure 14:
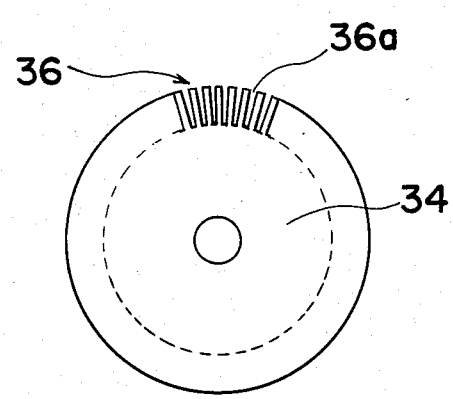
FIG. 14 is a plan view, on a somewhat enlarged scale, of the rotary disintegrator.

Further in the modification shown in FIG. 9, as a perforated gas distributor, a pipe 33 is utilized in place of the perforated ring pipe 32. This pipe 33 having one end communicated with the gas source 50 extends fluidtightly through the bottom wall of the vessel 30 with the other open end terminating immediately below the central region of the rotary disintegrator 34. Moreover, in the modification shown in FIG. 9, an additional rotary disintegrator 35 identical with the rotary disintegrator 34 may be employed together with an additional set of baffle plates 41, identical with the baffle plates 40, and a corresponding gas supply pipe 31 identical with the gas supply pipe 33, as shown in FIG. 9.

Although the baffle plates have been described as composed of generally elongated rectangular flat plates, they may be composed by coiled piping if it serves the purpose of disturbing the whirling of the ascending current of liquid medium to rectify it in a direction longitudinally of the vessel 30.

In any event, this invention is essentially featured in that the gas-liquid contacting apparatus having the perforated gas distributor within the vessel is provided with the rotary disintegrator positioned above the perforated gas distributor and having defined therein the apertures through which the bubbles of the gaseous medium can pass. In this construction, when the liquid medium L is placed in the vessel 30 and the gaseous medium is supplied into the liquid medium L within the vessel 30 while the rotary disintegrator 34 is rotated in one direction, the gaseous medium so supplied forms the bubbles which in turn form the vortex beneath the rotary disintegrator 34. As the outer upper portion of the vortex of the bubbles moves upwardly through the apertures 36 in the rotary disintegrator 34 being then rotated, the bubbles are cut and, therefore, disintegrated by the rotary disintegrator 34 into the fine bubbles which are in turn distributed into the liquid medium L above the rotary disintegrator 34.

EXPERIMENT 1

Figure 2:
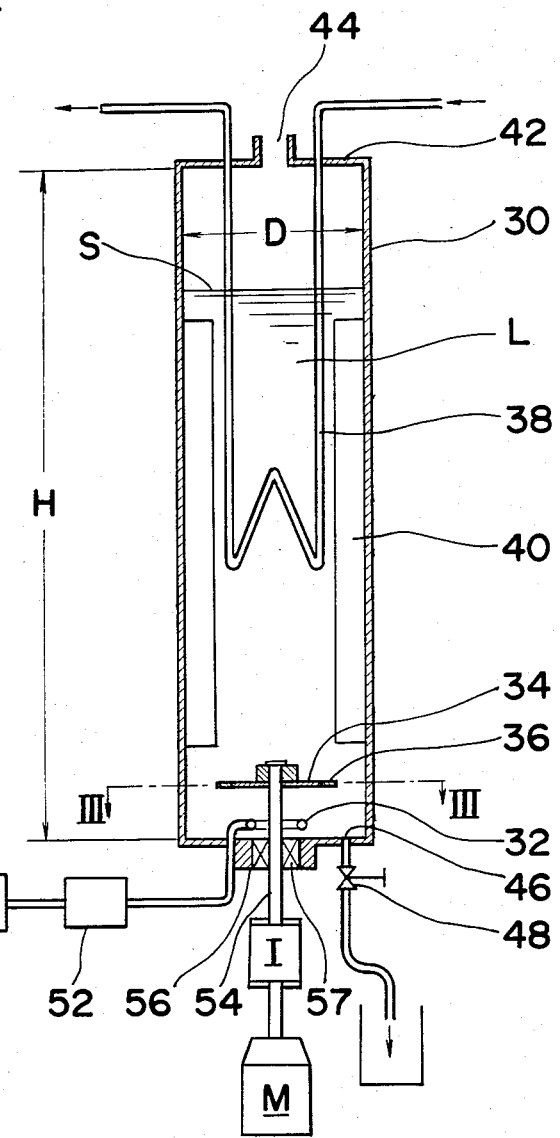
FIG. 2 is a schematic longitudinal sectional view of a gas-liquid contacting apparatus according to a first embodiment of this invention.

With the use of the gas-liquid contacting apparatus shown in FIG. 2, a series of experiments were carried out to air-oxidize a solution of 5 w/v% sodium sulfite. The results of the experiments are tabulated in Table 1 and shown in the graph of FIG. 7.

(1) Specifications of the gas-liquid contacting apparatus used were as follows:
Vessel 30: 145 mm $\phi$ and 1,000 mm in height H
Ring pipe 32: 50 mm in diameter with 5 perforations of 1.0 mm in diameter and made of a stainless pipe of 5 mm in bore size.
Rotary disintegrator 34:
  Type A: 100 mm diameter disc having 72 slits of FIG. 4 each being 2 mm in width and 10 mm in depth.
  Type B: 140 mm diameter disc having 74 slits of FIG. 4 each being 2.5 mm in width and 8 mm in depth.
  Type C: 140 mm diameter disc having 360 through-holes of FIG. 6 each being 2.4 mm in diameter.

(2) Operating conditions are as follows:
Concentration of Sodium Sulfite . . . 5 w/v%
Amount of Catalyst ($CuSO_4.5H_2O$) added . . . 0.001 mol
Amount of Charge in Vessel . . . 10 l
Air Supply Rate . . . 10 l/min (1 VVM)
Number of Revolution of Disintegrator 34 . . . 800–1600 rpm.
Reaction Temp. . . . 30° C.
Assay . . . iodometry Assay . . .

(3) The oxygen transfer rate (OTR) was calculated from the following equations.

$$OTR = \frac{C1 - C2}{2(\theta 2 - \theta 1)}$$

wherein
  OTR: Oxygen transfer rate in g-mol/ml min.
  C1 and C2: Concentrations (g-mol/ml) of $Na_2SO_3$ at respective times $\theta 1$ and $\theta 2$
  $\theta 1$ and $\theta 2$: Sampling times.

The stirrer power required was measured by the use of a rotary torque-meter and was calculated from the following equation.

$$Pg = \frac{1.027 \times 10^{-6} \times R \times (t - t0)}{V}$$

wherein
  Pg: Stirring power ($KW/m^3$)
  R: Number of revolution (rpm)
  t: Measured torque (g-m)
  t0: Measured torque (g-m)
  v: Quantity of liquid charged ($m^3$)

(3) Results:

TABLE 1

| Type of Disintegrator | Sum of Surface areas of Apertures 36 ($cm^2$) | PRM of Disintegrator | OTR (g-mol $O^2$/ $m^3$ Hr) | Stirring power ($KW/m^3$) | Oxygen Transfer Efficiency (g-mol $O^2$/ KWHr) |
|---|---|---|---|---|---|
| A | 14.4 | 1200 | 265.5 | 1.07 | 248.1 |
| A | 14.4 | 1400 | 365.5 | 1.66 | 220.2 |
| A | 14.4 | 1600 | 412.4 | 2.21 | 186.6 |
| B | 14.8 | 900 | 282.3 | 1.24 | 227.7 |
| B | 14.8 | 1000 | 336.6 | 1.98 | 170.0 |
| B | 14.8 | 1200 | 432.9 | 3.79 | 114.2 |
| C | 16.2 | 1000 | 261.4 | 1.28 | 204.2 |
| C | 16.2 | 1200 | 336.9 | 1.90 | 177.3 |

Note that the oxygen transfer efficiency is a ratio of the stirring power relative to OTR.

Figure 7:
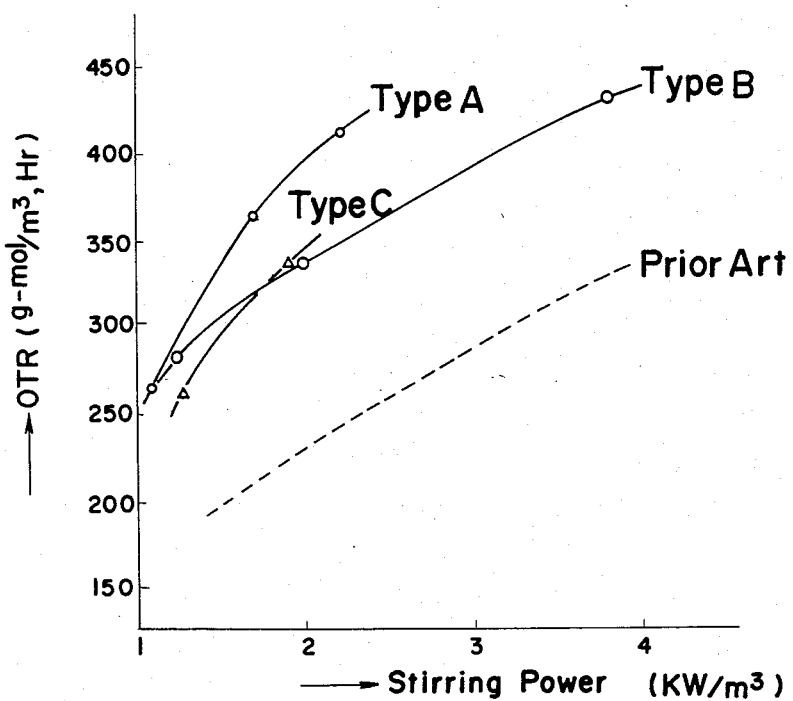
FIG. 7 is a graph showing the relationship in the apparatus of FIG. 2 between the oxygen transfer rate and the stirring power.

The relationship between the OTR and the stirring power for each different type of rotary disintegrator 34 at an air supply rate of 1 VVM under atmospheric condition is plotted in the graph of FIG. 7 together with that exhibited by the prior art gas-liquid contacting apparatus. From the results of the experiments, it is clear that, as compared with the prior art apparatus. The apparatus of this invention is effective to disintegrate the bubbles into fine bubbles at the reduced stirring power.

SECOND EMBODIMENT (FIGS. 11 TO 26)

Referring now to FIGS. 11 to 16, the gas-liquid contacting apparatus shown therein comprises, in addition to the numerous elements described and shown in connection with the preceding embodiment of this invention, a combination of a stirrer blade 60 and a draft tube 62 for circulating the liquid medium L within the vessel 30.

The stirrer blade 60 is rigidly mounted on the drive shaft 54 for rotation together therewith, which drive shaft 54 extends downwards from the motor M through a bearing 57 on the lid 42 and then concentrically through the draft tube 62, and terminates in rotatable engagement with the bearing 56. While the rotary disintegrator 34 is mounted on the drive shaft 54 at a position adjacent the bottom of the vessel 30 and above the open end of the gas supply pipe 33, the stirrer blade 60 is mounted on the drive shaft 54 at a substantially intermediate portion thereof and adjacent a lower open end of the draft tube 62 supported within the vessel 30 in a manner as will now be described.

The draft tube 62 is in the form of a cylindrical hollow body having its opposite ends open and is generally concentrically supported within the vessel 30 by means of a plurality of pairs of arm members 64, each extending between the baffle plate 40 and the outer periphery of the draft tube 62, with the lower open end spaced a predetermined distance upwardly from the level of the rotary disintegrator 34 and with the opposite, upper open end held generally flush with or slightly beneath the top surface level S of the liquid medium L contained in the vessel 30. This draft tube 30 has a predetermined diameter Dd and a predetermined height Hd which satisfy the following relationships relative to the diameter DT and the height HT of the vessel 30:

$$0.8 \geq Dd/DT \geq 0.1$$

$$0.8 \geq Hd/Ht \geq 0.2$$

In addition, the upper open end of the draft tube 62 must, as hereinbefore described, be held generally flush with or slightly beneath the top surface level S of the liquid medium L so that, when the gaseous medium is supplied into the liquid medium in the form of the bubbles from the gas supply pipe 33 in the manner as hereinbefore described in connection with the first embodiment, the top surface level S can be carried to a level higher than the level of the upper open end of the draft tube 62 to allow the liquid medium to flow into or out of the draft tube 62. Although the gas supply rate and/or the stirring condition will dominate the extent to which the top surface level S of the liquid medium L within the vessel 30 is upwardly shifted during the operation of the apparatus, it would be about 5 to 30%.

Figure 15:
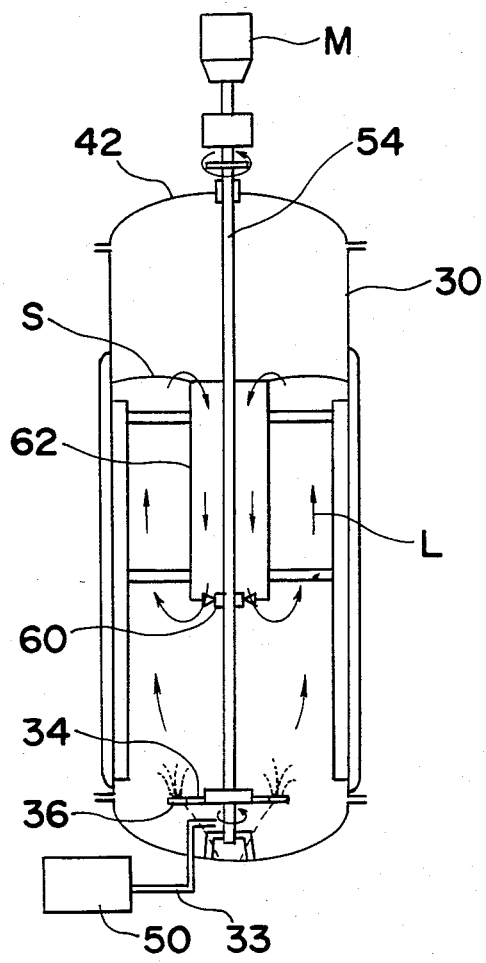
FIGS. 15 and 16 are schematic diagrams of the apparatus of FIG. 11, showing different modes of operation thereof.
Figure 16:
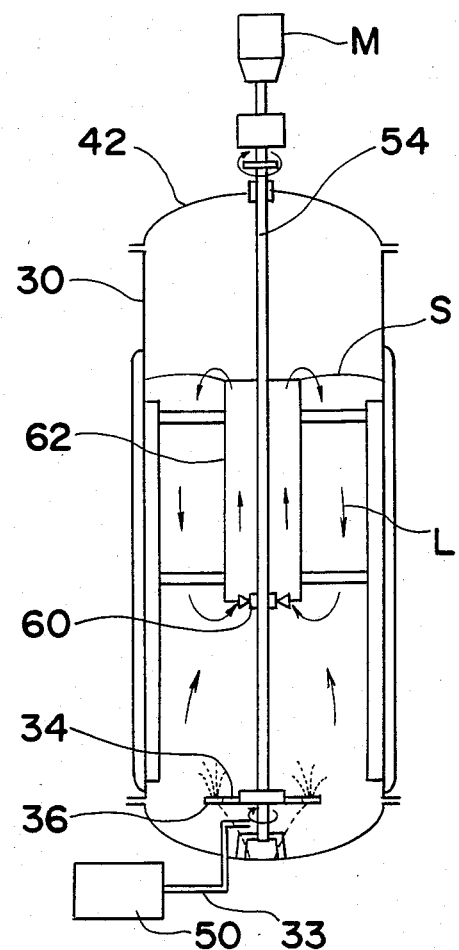

The stirring blade 60 is constituted by a propeller blade having a high discharge rate and serves to stir the liquid medium L and also to assist and promote the circulation of the liquid medium L. Specifically, when the stirrer blade 60 is rotated in one direction as shown in FIG. 15, the liquid medium L within the draft tube 62 flows so as to emerge downwardly from the lower open end of the draft tube 62 while the liquid medium exteriorly of the draft tube 62 is caused to flow over the uppr open end of the draft tube 62 into the inside of the draft tube 62 as shown by the arrows in FIG. 15. However, as shown in FIG. 16, when the stirrer blade 60 is rotated in the reverse direction, the pattern of circulation of the liquid medium relative to the draft tube is also reversed from that shown in FIG. 15. Thus, it will readily be seen that, during the rotation of the stirrer blade 60, the liquid medium is forcibly circulated within the vessel 30 to allow the bubbles, which have been disintegrated by the rotation of the rotary disintegrator 34, to be uniformly dispersed in liquid medium L. In addition, the rotation of the stirrer blade 60 can bring about a defoaming effect in a manner as will subsequently be described.

Specifically, during the rotation of the stirrer blade 60 in said one direction as shown in FIG. 15, the foams floating on the top surface of the liquid medium are forced to enter the draft tube 62 together with the liquid medium over flowing into the inside of the draft tube 62 in the manner as hereinbefore described and, therefore, the foams can be defoamed. On the other hand, during the rotation of the stirrer blade 60 in the reverse direction as shown in FIG. 16, the liquid medium forced to overflow from the inside of the draft tube 60 towards the exterior of the draft tube 62 in the manner as hereinbefore described splashes onto the foams floating on the top surface of the liquid medium, thereby defoaming the foams in a manner similar to that exhibited by showering the liquid from the defoaming nozzle in the prior art apparatus shown in FIG. 1.

The gas-liquid contacting apparatus described with reference to and shown in FIGS. 11 to 16 can be modified in a number of ways as shown in FIGS. 18 to 26.

Figure 18:
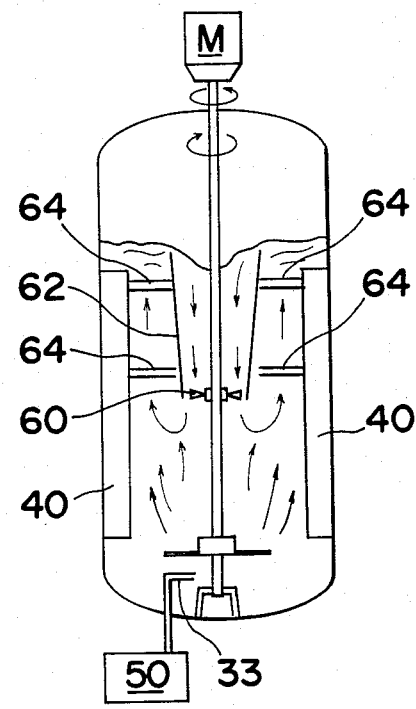
FIGS. 18 to 20 are views similar to FIG. 11, showing respective modified forms of the apparatus of FIG. 11.

Referring to FIG. 18, the draft tube 62 is shown as tapering from the upper open end towards the lower open end. In this case, the tapering draft tube 62 should be so dimensioned as to satisfy the following requirements relative to the vessel 30:

$$0.3 < Dd2/Dd1 < 1.0$$
and
$$0.6 < Dd1/Dt < 0.2$$

wherein
Dd1: diameter of the upper open end of the draft tube 62
Dd2: Diameter of the lower open end of the draft tube 62
Dt: Inner diameter of the vessel 30.

Figure 19:
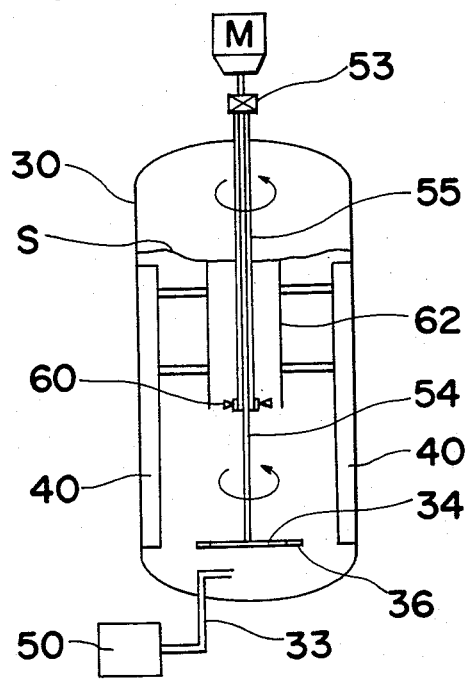

In the modification shown in FIG. 19, a drive shaft 55 separate from the drive shaft 54 for rotating the rotary disintegrator 34 is employed for driving the stirrer blade 60. For this purpose, the drive shaft 55 is in the form of a quill shaft loosely surrounding the drive shaft 54 and having a lower end carrying the stirrer blade 60 and an upper end drivingly coupled to the drive shaft through a reduction gear mechanism 53. Preferably, the reduction gear mechanism 53 is of such a design that the stirrer blade 60 can be rotated at a speed different from, for example, lower than, the speed of rotation of the rotary disintegrator 34.

Figure 20:
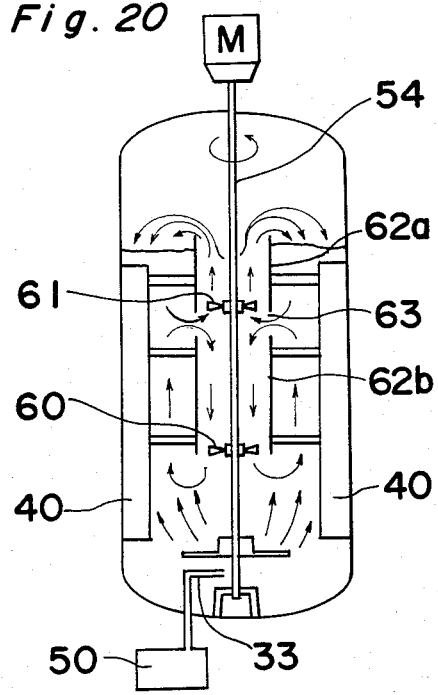

In the modification shown in FIG. 20, the draft tube is divided into coaxially aligned, upper and lower tube components 62a and 62b with an annular space 63 defined therebetween, and an additional stirrer blade 61 similar to the stirrer blade 60 adjacent the lower open end of the tube component 62b is employed. The stirrer blade 61 is so designed and so positioned adjacent the lower open end of the upper tube component 62a and above the lower tube component 62b that, while the stirrer blade 60 during its rotation together with the drive shaft 54 serves to circulate the liquid medium, drawing the liquid medium interiorly from the annular space 63 into the hollow of the lower tube component 62b and then allowing it to flow upwards exteriorly of the tube component 62b after having flowed downwards through the hollow of the lower tube component 62b, the additional stirrer blade 61 can, during its rotation together with the same drive shaft 54 in the same direction, establish at an upper region around the upper tube component 62a, a pattern of circulation generally reverse to that established by the stirrer blade 60. In this design shown in FIG. 20, the stirrer blade 60 substantially plays the role of stirring the liquid medium to allow the disintegrated bubbles to be uniformly dispersed in the liquid medium whereas the additional stirrer blade 61 plays the role of splashing the circulated liquid medium over onto the top surface S of the liquid medium to defoam the foams floating thereon.

In the modified arrangements shown in FIGS. 21 and 22, 23 and 24, and 25 and 26, the vessel 30 of the construction shown in FIG. 20 is provided with a different type of foam suppressing element for minimizing the formation of foams.

Figure 21:
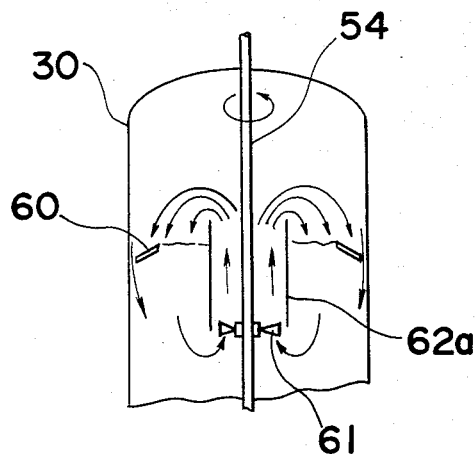
FIGS. 21, 23 and 25 are fragmental sectional views of an upper portion of the apparatus of FIG. 11, showing different types of foam suppressing elements used therein.
Figure 22:
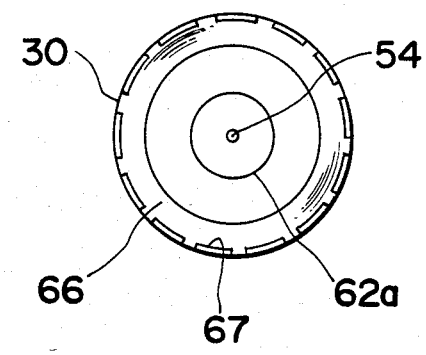
FIGS. 22, 24 and 26 are cross-sectional views of FIGS. 21, 23 and 25, respectively.

The foam suppressing element shown in FIGS. 21 and 22 comprises an annular cover plate 66 secured at its outer periphery to the inner wall surface of the vessel 30 and having in its outer peripheral portion a plurality of circumferentially equally spaced cutouts 67. This annular cover plate 66 serves to guide the circulation of the liquid medium through the tube component 62a and also to minimize the surface area of the top surface S of the liquid medium which contacts the air contained in the top of the vessel 30 thereby to supress the formation of the foams.

Figure 23:
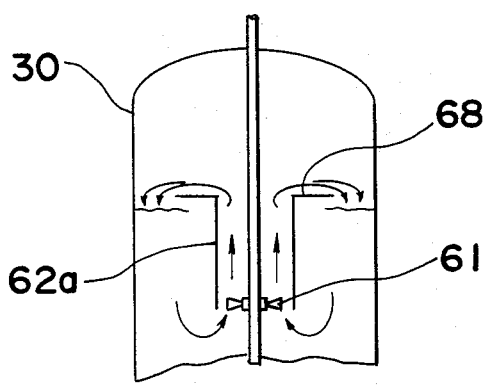
Figure 24:
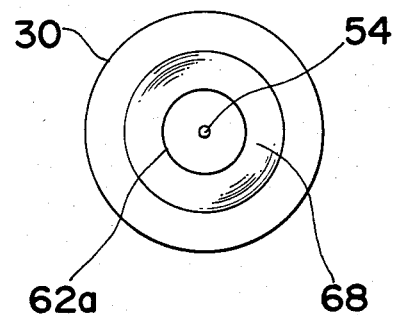

In the example shown in FIGS. 23 and 24, the foam suppressing element comprises as annular flange 68 integrally formed with the tube component 62a and extending radially outwardly from the upper end of the tube component 62a. This annular flange 68 can function in a manner similar to the annular cover plate 66 shown in FIGS. 21 and 22.

Figure 25:
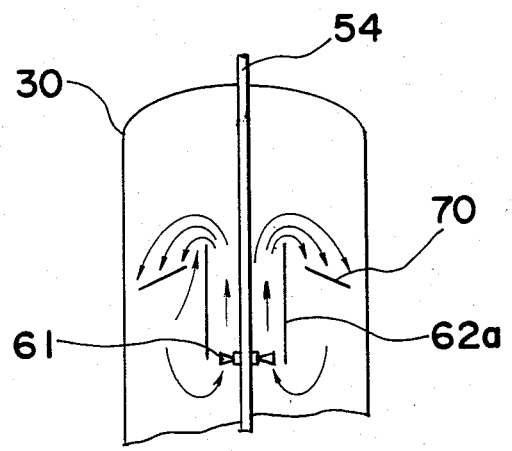
Figure 26:
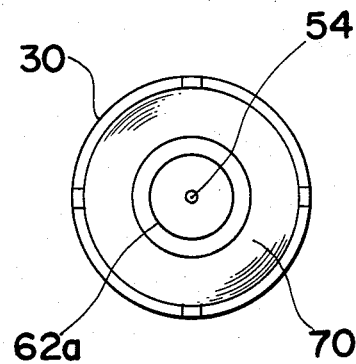

In the example shown in FIGS. 25 and 26, the foam suppressing element comprises a bevel-shaped annular cover plate 70 secured to the vessel 30 in a manner similar to the annular cover plate 66 shown in FIGS. 21 and 22 and capable of functioning in a manner similar to the annular cover plate 66 shown in FIGS. 21 and 22.

The gas-liquid contacting apparatus according to the second embodiment of this invention functions in a manner similar to the apparatus according to the first embodiment thereof. However, one thing to note is that, because of the employment of the draft tube 62 and the stirrer blade 60, the bubbles which have been disintegrated into fine bubbles by the action of the rotary disintegrator 34 in the manner as hereinbefore described, particularly in connection with the first embodiment of this invention, can further be dispersed uniformly in the liquid medium within the vessel 30 by the effect of the forced circulation achieved by the stirrer blade 60 in cooperation with the draft tube 62.

Specifically, since the liquid medium within the vessel 30 is forced to circulate slowly interiorly and exteriorly of the draft tube 62 by the action of the stirrer blade 60, the disintegrated bubbles can ride on this circulating flow of the liquid medium and, therefore, be substantially uniformly dispersed therein. At this time, although the stirrer blade 60 accelerates the circulation of the liquid medium through the draft tube 62, it will not substantially participate in the disintegration of the bubbles and, therefore, the energy consumption of the stirrer blade 60 required for breaking the bubbles can be of a negligible value.

As hereinabove described, in the apparatus according to the second embodiment of this invention, the disintegration of the bubbles into fine bubbles by the action of the rotary disintegrator 34 and the forced circulation of the liquid medium to agitate the liquid medium take place substantially simultaneously at the lower and upper regions, respectively, of the vessel 30.

Figure 27:
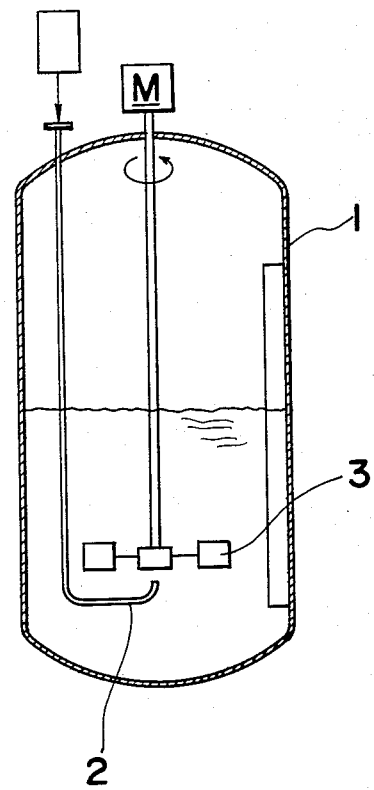
FIG. 27 is a schematic longitudinal sectional view of another prior art gas-liquid contacting apparatus used.

As compared with the prior art apparatus comprising, as shown in FIG. 27, a vessel 1 having a gas supply pipe 2 disposed within the vessel 1 near the bottom thereof for the supply of the gaseous medium and a turbine blade 3 disposed within the vessel above the supply pipe 2 for disintegrating the bubbles of the gaseous medium discharged from the supply pipe 2 and also for stirring and circulating the liquid medium within the vessel 1, the apparatus according to the second embodiment of this invention is such that, when it is used as a fermentation means, for a given quantity of energy required to stir the liquid medium, the oxygen transfer rate increases, and, in the case of aerobic cultivation, results in accelerated fermentation and the productivity consequently increases. In addition, because of the increased oxygen transfer rate, fermentation using a culture medium which contains a substrate of a nature tending to hamper the dissolution of oxygen results in the increased concentration of the substrate. Therefore, the apparatus according to this invention is effective for the cultivation with a high productivity.

Moreover, since a simple method is practised in the apparatus of this invention to defoam the foams floating on the top surface of the liquid medium, the number and occurrence of troubles attributable to the presence of the foams can advantageously be reduced as compared with that in the prior art apparatus of FIG. 27, and therefore, the length of time the liquid medium is held within the vessel can correspondingly be increased.

Hereinafter, experiments done to compare the apparatus according to this invention with the conventional one will be demonstrated only for the purpose of illustration.

EXPERIMENT 2

The prior art apparatus of the construction shown in FIG. 27 and the apparatus of the construction shown in FIGS. 11 to 14 were compared under the same condition as to the capacity coefficient connected with the oxygen transfer which had occurred during the air-oxidization of a sodium sulfite solution.

(1) Specifications of the apparatuses (a) Prior Art Apparatus (as shown in FIG. 27)

| Vessel: | Diameter | 0.53 m |
|---|---|---|
| | Volume | 0.2 m$^3$ |
| | Height | 1.10 m |
| | Quantity of Charge | 0.1 m$^3$ |

-continued

| Blade: | Type | Single-state, 6 element turbine blade |
| | No. of Blade Elements | 6 |
| | Diameter | 0.3 m |
| | Height | 0.06 m |
| | Width | 0.077 m |
| (b) Inventive Apparatus (as shown in FIGS. 11 to 14) | | |
| Vessel: | Diameter | 0.47 m |
| | Volume | 0.23 m$^2$ |
| | Height | 1.30 m |
| | Quantity of Charge | 0.18 m$^3$ |
| | Height of Liquid Column about the Disintegrator | 1.0 m |
| Draft Tube: | Diameter | 0.15 m |
| | Length | 0.5 m |
| | Wall Thickness | 3 mm |
| Upper open end: | Held in flush with the top level surface of the liquid in the vessel. | |
| Lower open end: | Spaced 0.5 m upwardly from the level of the disintegrator. | |
| Baffle Plates: | Length | 0.9 m |
| | Width | 0.07 m |
| Stirrer Blade: | Diameter | 0.10 m |
| Disintegrator: | Diameter | 0.25 m |
| | Plate Thickness | 4 mm |
| | Material | sus |
| | Slit Width | 3 mm |
| | Slit Depth | 30 mm |
| | Slit Number | 120 |
| (2) Operating Conditions: | | |
| Concentration of Sodium Sulfite | | 5 w/v % |
| Amount of Catalyst (CuSO$_4$.5H$_2$O) added | | 0.001 mol |
| Air Supply Rate | | 1 VVM |
| Pressure inside Vessel (P) | | 1 kg/cm$^2$ G |
| Reaction Temp. | | 30° C. |

(3) Calculating Equations (a) The capacity coefficient connected with the oxygen transfer is calculated by the use of the following equations.

$$Kd = \frac{OTR}{plm}$$

$$OTR = \frac{C1 - C2}{2(\theta 2 - \theta 1)}$$

wherein
Kd: Capacity coefficient (g-mol O$_2$/m$^3$ hr atm)
OTR: Oxygen transfer rate (g-mol O$_2$/m$^3$ hr)
C1 and C2: Concentrations of Na$_2$SO$_3$ at respective times $\theta 1$ and $\theta 2$.
plm: Average logarithmic value of oxygen partial pressure at inlet and outlet
$\theta 1$ and $\theta 2$: Sampling times.
(b) The stirring power required was measured by the use of a rotary torque-meter and was then calculated from the following equation.

$$Pg = \frac{1.027 \times 10^{-6} \times R \times (t - t0)}{V}$$

wherein
Pg: Stirring power (Kw/m$^3$)
R: Number of revolution (rpm)
t: Measured torque (g-m)
t0: Measured torque (g-m) when the vessel is empty.
V: Quantity of liquid charged (m$^3$)

(4) RESULTS

Figure 17:
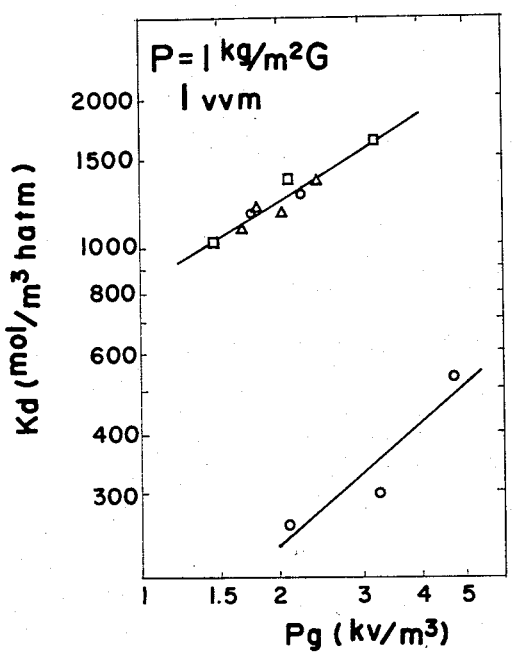
FIG. 17 is a graph showing the relationship in the apparatus of FIG. 11 between the oxygen transfer capacity coefficient and the stirring power.

The results of the experiments are tabulated in Table 2 and the oxygen transfer capacity coefficient Kd (mol/m$^3$.hr.atm) exhibited by the prior art apparatus and that by the apparatus of this invention are plotted in the graph of FIG. 17.

TABLE 2

| | Invention | | | Prior Art | | |
|---|---|---|---|---|---|---|
| Stirring Speed (rpm) | 620 | 620 | 700 | 150 | 175 | 200 |
| Blade Peripheral Velocity of Blade (m/sec) | 8.1 | 8.1 | 9.2 | 2.4 | 2.7 | 3.1 |
| Air Supply Rate (VVM) | 1 | 1 | 1 | 1 | 1 | 1 |
| Reaction Pressure (kg/cm$^2$) | 1 | 2 | 2 | 2 | 2 | 2 |
| Stirring Power (Kw/m$^3$) | 1.36 | 1.86 | 2.44 | 2.08 | 3.28 | 4.72 |
| OTR (g-mol/m$^3$ · hr) | 254 | 343 | 375 | 100 | 114 | 177 |
| Kd (g-mol/m$^3$ · hr · atm) | 1513 | 1200 | 1383 | 260 | 302 | 561 |

From the foregoing, it is clear that, in the case where the stirring power is 3 Kw/m$^3$, the oxygen transfer capacity coefficient exhibited by the apparatus of this invention has increased to a value about 5 times higher than that of the prior art apparatus of FIG. 27 and that the efficiency of charge of the liquid medium into the vessel has also increased to a value about 80% higher than that exhibited by the prior art apparatus. This in turn makes it clear that the employment of the combination of the draft tube with the stirrer blade playing the different roles as hereinbefore fully described renders the apparatus of this invention to be superior to the prior art apparatus. This is also evidenced by the following experiments which were conducted to demonstrate the advantage of the combined use of the draft tube and the stirrer blade.

EXPERIMENT 3

(1) Using the two apparatuses of the invention, one equipped with the draft tube and the stirrer blade (hereinafter referred to as a "model A") and the other without both of the draft tube and the stirrer blade (hereinafter referred to as a "model B"), the experiments were conducted. For this purpose, while the models A and B have a construction substantially identical with that used in the Experiment 2, the rotary disintegrator employed in each of these models A and B had the following dimensions and design.
Diameter . . . 200$\phi$
Slit Width . . . 3 mm
Slit Depth . . . 15 mm
Slit Number . . . 90

(2) RESULTS

The results of experiments are tabulated in Table 3.

TABLE 3

| | Model A | | | Model B | | |
|---|---|---|---|---|---|---|
| Stirring Speed (rpm) | 880 | 930 | 980 | 880 | 930 | 980 |
| Blade Peripheral Velocity (m/sec) | 9.2 | 9.7 | 10.3 | 9.2 | 9.7 | 10.3 |
| Air Supply Rate (VVM) | 1 | 1 | 1 | 1 | 1 | 1 |
| Reaction Pressure (kg/cm$^2$) | 2 | 2 | 2 | 2 | 2 | 2 |
| Stirring Power (Kw/m$^3$) | 1.45 | 1.75 | 2.24 | 0.94 | 1.50 | 1.85 |
| OTR (g-mol/m$^3$ · hr) | 309 | 341 | 357 | 247 | 262 | 302 |
| Kd (g-mol/m$^3$ · hr · atm) | 1015 | 1184 | 1274 | 743 | 806 | 975 |

From Table 3, it is clear that the employment of the draft tube and the stirrer blade has resulted in the increase of the oxygen transfer capacity coefficient Kd to a value about 30% higher than that exhibited by the apparatus without the both.

EXPERIMENT 4

(1) In this experiment, a qualitative comparison was made to determine the defoaming effect within the vessel, using the two types of the apparatuses of the construction substantially shown in FIGS. 11 to 14, one equipped with the draft tube and the stirrer blade and the other not equipped with the draft tube and the stirrer blade.

(2) OPERATING CONDITIONS

Type of liquid used: Water
Foaming agent: 0.004% cleaning agent
Air Supply Rate: 180 l-air/min.
Quantity of Water: 120–180 l

(3) PROCEDURES

With respect to the apparatus (model X) without both the draft tube and the stirrer blade, the apparatus (model Y) with both of the draft tube and the stirrer blade, and having the drive shaft 54 rotated in one direction as shown in FIG. 15, and the apparatus (model Z) with both of the draft tube and the stirrer blade and having the drive shaft 54 rotated in the reverse direction as shown in FIG. 16, the quantity of water charged in the respective vessel was adjusted so as to be within the range of 120 to 180 l to determine the efficiency or percentage of charge of water in the respective vessel at which the respective apparatus is operable.

(4) RESULTS

The results of the experiments are tabulated in Table 4.

TABLE 4

| Efficiency of Charge (%) | Model X | Model Y | Model Z |
|---|---|---|---|
| 50 | Operable | | |
| 60 | Operable | Operable | |
| 70 | Not operable | Operable | Operable |
| 80 | Not operable | Not operable | Operable |
| 90 | Not operable | Not operable | Not operable |

From the Table 8, it is clear that, as compared with the model X, the use of the draft tube in combination with the stirrer blade such as in both models Y and Z has exhibited an increased defoaming effect. In particular, where in the model Z the defoaming effect is greater than in the model Y.

Figure 28:
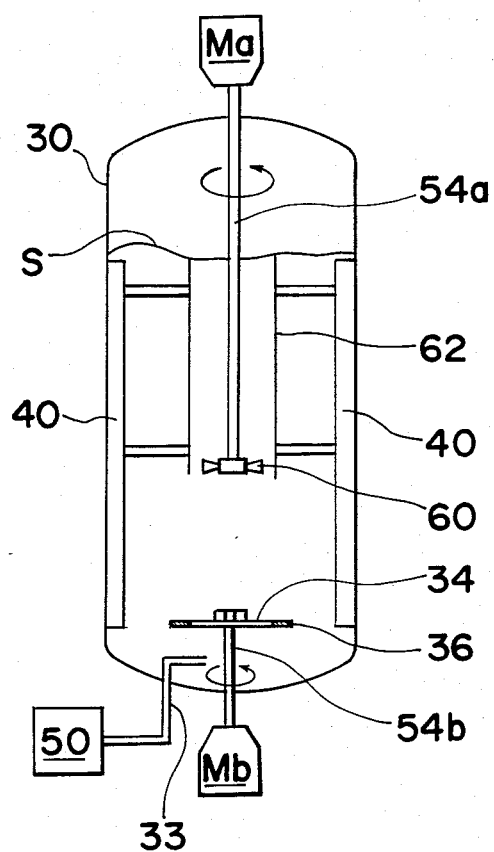
FIG. 28 is a view similar to FIG. 27, showing a further modified form of the apparatus according to this invention.

Although this invention has fully been described in connection with the preferred embodiments with reference to the accompanying drawings, it is to be noted that various changes and modifications will be apparent to those skilled in the art. By way of example, in the second embodiment including its various modifications, two electric motors may be employed for separately driving the rotary disintegrator and the stirrer blade together with their respective drive shafts. In this case, one of the motors, Mb, for the rotary disintegrator and the other, Ma, for the stirrer blade should be positioned below and above the vessel, respectively, as shown in FIG. 28. Alternatively, even through separate drive shafts 54a and 54b are employed for the rotary disintegrator and the stirrer blade, respectively, one drive motor can be used for driving both of the separate drive shafts. In this case, a gear train, a belt drive system or any other suitable drive transmission system is required to accomplish it.

Accordingly, such changes and modifications are to be understood as being included within the true scope of this invention as defined by the appended claims unless they depart therefrom.

What is claimed is:

1. A gas-liquid contacting apparatus which comprises, in combination:
    a generally cylindrical upright vessel for accommodating a quantity of liquid medium to be agitated by the action of bubbles of gaseous medium moving upwards within the vessel;
    at least one perforated distributor in said vessel for supplying the gaseous medium under pressure into the vessel so as to disperse it into the liquid medium in the form of bubbles;
    at least one generally disc-shaped rotary disintegrator rotatably mounted in said vessel immediately above said distributor for rotation in a plane perpendicular to the longitudinal axis of said vessel and concentric with the inner peripheral surface of said vessel and having a diameter for defining an annular clearance between the periphery of said disintegrator and the inner peripheral surface of said vessel, said disintegrator having a flat under surface facing the bottom of said vessel for, during the rotation of said disintegrator, causing bubbles of the gaseous medium emerging from said distributor to form a vortex below the flat under surface of said disintegrator, said distributor having a plurality of apertures therein in an annular area around the outer peripheral part of said disintegrator, the radial dimension of said annular area being less than half the radius of said disintegrator, and each of said apertures extending completely through the thickness of said disintegrator from said flat under surface to the upper surface thereof and being defined by peripheral edges of said disintegrator around said apertures, whereby all the bubbles from said vortex pass upwards through the apertures and are sheared by the peripheral edges of said disintegrator for disintegrating the bubbles into fine bubbles;
    a drive shaft extending coaxially into said vessel and having one end positioned exteriorly of said vessel and having said disintegrator mounted on the other end for rotation together with said shaft; and
    a drive mechanism connected to said one end of said drive shaft.

2. An apparatus as claimed in claim 1 further comprising baffle means disposed along the inner peripheral surface of said vessel parallel to said longitudinal axis and above said disintegrator for providing resistance to the whirling flow of the liquid medium with the disintegrated bubbles therein which occur as a result of rotation of said disintegrator.

3. An apparatus as claimed in claim 1 wherein each of said apertures is a slit opening out of the peripheral edge of said disintegrator.

4. An apparatus as claimed in claim 1 wherein said each of said apertures is a through hole.

5. An apparatus as claimed in claim 1 wherein the ratio of the total surface area of said disintegrator to the sum of the cross-sectional areas of the respective apertures is in the range of 0.05 to 0.35.

6. An apparatus as claimed in claim 1 wherein each of said apertures is no larger than 20 mm in size.

7. An apparatus as claimed in claim 1 wherein said drive mechanism comprises an electric motor mounted above said vessel and said drive shaft extends downward therefrom into said vessel.

8. An apparatus as claimed in claim 1 further comprising at least one further distributor and disintegrator are mounted in said vessel above said firstmentioned distributor and disintegrator to form a second stage for disintegration of bubbles.

9. An apparatus as claimed in claim 1 further comprising means for journalling said drive shaft at the top and the bottom of said vessel.

10. A gas-liquid contacting apparatus which comprises, in combination:
- a generally cylindrical upright vessel for accomodating a quantity of liquid medium to be agitated by the action of bubbles of gaseous medium moving upwards within the vessel;
- at least one perforated distributor in said vessel for supplying the gaseous medium under pressure into the vessel so as to disperse it into the liquid medium in the form of bubbles;
- at least one generally disc-shaped rotary disintegrator rotatably mounted in said vessel immediately above said distributor for rotation in a plane perpendicular to the longitudinal axis of said vessel and concentric with the inner peripheral surface of said vessel and having a diameter for defining an annular clearance between the periphery of said disintegrator and the inner peripheral surface of said vessel, said disintegrator having a flat under surface facing the bottom of said vessel for, during the rotation of said disintegrator, causing bubbles of the gaseous medium emerging from said distributor to form a vortex below the flat under surface of said disintegrator, said distributor having a plurality of apertures therein in an annular area around the outer peripheral part of said disintegrator, the radial dimension of said annular area being less than half the radius of said disintegrator, and each of said apertures extending completely through the thickness of said disintegrator from said flat under surface to the upper surface thereof and being defined by peripheral edges of said disintegrator around said apertures, whereby all the bubbles from said vortex pass upwards through the apertures and are sheared by the peripheral edges of said disintegrator for disintegrating the bubbles into fine bubbles;
- a drive shaft extending coaxially into said vessel and having one end positioned exteriorly of said vessel and having said disintegrator mounted on the other end for rotation together with said shaft;
- a drive mechanism connected to said one end of said drive shaft;
- a draft tube mounted in said vessel coaxially thereof and above said disintegrator; and
- at least one rotary stirrer cooperable with said draft tube for producing a circulation of the flow of liquid medium within said vessel through the interior of said draft tube and then through the space between said draft tube and the inner peripheral surface of said vessel by the rotation of said stirrer.

11. An apparatus as claimed in claim 10 in which said stirrer is mounted on said drive shaft for rotation therewith.

12. An apparatus as claimed in claim 10 further comprising baffle means disposed along the inner peripheral surface of said vessel parallel to said longitudinal axis and above said disintegrator for providing resistance to the whirling flow of the liquid medium with the disintegrated bubbles therein which occur as a result of rotating said disintegrator.

13. An apparatus as claimed in claim 10 wherein each of said apertures is a slit opening out of the peripheral edge of said disintegrator.

14. An apparatus as claimed in claim 10 wherein each of said apertures is a through hole.

15. An apparatus as claimed in claim 10 further comprising means for reversing the direction of drive to said stirrer.

16. An apparatus as claimed in claim 10 wherein said draft tube is tapered downwardly and inwardly of said vessel.

17. An apparatus as claimed in claim 10 further comprising an additional drive shaft connected to said stirrer by means of which said stirrer is driven.

18. An apparatus as claimed in claim 10 further comprising a further drive mechanism connected to said stirrer for driving said stirrer.

19. An apparatus as claimed in claim 10 further comprising at least one further distributor and disintegrator and at least one further draft tube and stirrer, all mounted in said vessel above said firstmentioned distributor, disintegrator, draft tube and stirrer.

20. An apparatus as claimed in claim 10 further comprising a generally annular foam suppressing element positioned within said vessel above said draft tube.

* * * * *

UNITED STATES PATENT AND TRADEMARK OFFICE
CERTIFICATE OF CORRECTION

PATENT NO. : 4,519,959

DATED : May 28, 1985

INVENTOR(S) : Tatsuro Takeuchi, Shohei Yoshida and Kazuhiro Kawai

It is certified that error appears in the above-identified patent and that said Letters Patent is hereby corrected as shown below:

Column 18, line 29: for "distributor" read --disintegrator--.

Column 19, line 34: for "distributor" read --disintegrator--.

Signed and Sealed this

Twenty-fourth Day of September 1985

[SEAL]

Attest:

Attesting Officer

DONALD J. QUIGG

Commissioner of Patents and Trademarks—Designate